(12) United States Patent
Steinman

(10) Patent No.: US 6,794,414 B1
(45) Date of Patent: Sep. 21, 2004

(54) METHOD AND COMPOSITIONS FOR TREATING DISEASES MEDIATED BY TRANSGLUTAMINASE ACTIVITY

(75) Inventor: Lawrence Steinman, Palo Alto, CA (US)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/719,770

(22) PCT Filed: Jun. 17, 1999

(86) PCT No.: PCT/US99/13615

§ 371 (c)(1),
(2), (4) Date: Sep. 6, 2001

(87) PCT Pub. No.: WO99/65516

PCT Pub. Date: Dec. 23, 1999

Related U.S. Application Data
(60) Provisional application No. 60/089,603, filed on Jun. 17, 1998.

(51) Int. Cl.$^7$ .................. A61K 31/13; A61K 31/19; A61K 31/21; A61K 31/195; A61K 31/175
(52) U.S. Cl. ................ 514/665; 514/506; 514/513; 514/557; 514/561; 514/579; 514/592; 514/603; 424/630
(58) Field of Search ..................... 514/603, 506, 514/513, 557, 561, 579, 592, 665; 424/630

(56) References Cited

U.S. PATENT DOCUMENTS 5,514,579 A    5/1996   O'Hara et al.

FOREIGN PATENT DOCUMENTS

| WO | WO 92/13530 | * | 8/1992 |
| WO | WO 98/04245 | * | 2/1998 |
| WO | WO 99/65516 |   | 12/1999 |

OTHER PUBLICATIONS

Scherzinger et al., "Huntingtin–encoded polyglutamine expansions form amyloid–like protein aggregates in vitro and in vivo", *Cell*, 90:549–558 (Aug. 8, 1997).
Ciechanover et al., Commentary "The ubiquitin–proteasome pathway: The complexity and myriad functions of proteins death", *Proc. Natl. Acad. Sci. USA*, 95:2727–2730 (Mar. 1998).
Cooper et al., "Rapid Communication Polyglutamine domains are substrates of tissue transglutaminase: Does Transglutaminase play a role in expanded CAG/Poly–Q neurodegenarative diseases!", *Journal of Neurochemistry*, 69(1):431–434 (1997).
Jeon et al., "QTL influencing autoimmune diabetes and encephalomyelitis map to a 0.15–cM region containing 112", *Nature Genetics*, 21:158–160 (Feb. 1999).
Skinner et al., "Ataxin–1 with an expanded glutamine tract alters nuclear matrix–associated structures", *Nature*, 389:971–974 (Oct. 30, 1997).
Matilla et al., "The cerebellar leucine–rich acidic nuclear protein interacts with ataxin–1", *Nature*, 389:974–978 (Oct. 30, 1997).
Burke et al., "Huntingtin and DRPLA proteins selectively interact with the enzyme GAPDH", *Nature Medicine*, 2(3)347–350 (Mar. 1996).
Cariello et al., "Transglutaminase activity is related to CAG repeat length in patients with Huntington's disease", *Hum. Genet.*, 98:6330635 (1996).
Dieterich et al., "Identification of tissue transglutaminase as the anutoantigen of celiac disease", *Nature Medicine*, 3(7)797–801 (Jul. 1997).
Ciechanover, "The ubiquitin–proteasome proteolytic pathway", *Cell*, 79:13–21 (Oct. 7, 1994).
Steinmann, "Escape from "Horror Autotoxicus": Pathogenesis and treatment of autoimmune disease", *Cell*, 80:7–10 (Jan. 13, 1995).
Green, "Letter to the Editor Human genetic diseases due to codon reiteration: relationship to an evolutionary mechanism" *Cell*, 74:955–956 (Sep. 24, 1993).
Kahlem et al., "Peptides containing glutamine repeats as substrates for transglutaminase–catalyzed cross–linking: Relevance to diseases of the nervous system", *Proc. Natl. Acad. Sci, USA*, 93:14580–14585 (Dec. 1996).
Kahlem et al., "Transglutaminase action imitates Huntington's disease: Selective polymerization of Huntingtin containing expanded polyglutamine", *Molecular Cell*, 1:595–601 (Mar. 1998).
Abstract—Ferguson, "Use of transglutaminase modulators to promote healing of wounds and fibrotic disorders", *HCA-PLUS*, (1999).
Abstract—Chandradhekar et al., "Parasitic nematode transglutaminase proteins and nucleic acid molecules, and their uses for inhibitor screening and recombinant vaccines", *HCAPLUS* (1999).

* cited by examiner

Primary Examiner—Sreeni Padmanabhan
(74) Attorney, Agent, or Firm—Browdy and Neimark, PLLC

(57) ABSTRACT

Diseases Mediated by transglutaminase, such as Huntington's Disease, spinobulbar atrophy, spinocerebellar ataxia, and dentatorubralpallidoluysian atrophy, as well as inflammatory diseases of the central nervous system, including mautiple sclerosis, rheumatoid arthritis, and insulin dependent diabetes mellitus, can be treated by administering a transglutaminase inhibitor such as monadansyl cadaverine, monoamines and diamines such as cystamine, putrescine, GABA. (gamma-amino benzoic acid), N-benzyloxy carbonyl, 5-deazp-4-oxonorvaline p-nitrophenylester, glycine methyl ester, CuSO4, and the oral anti-hyperglycemic agent tolbutamide.

15 Claims, 9 Drawing Sheets

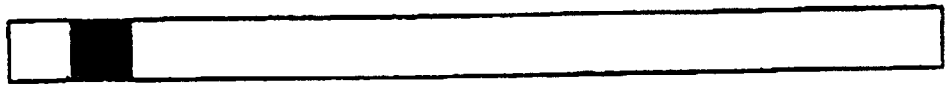
~310 aa
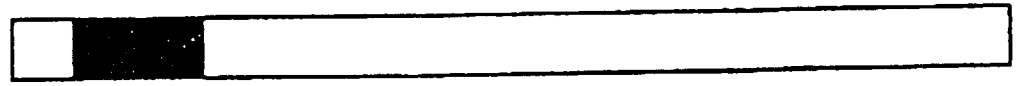
~330 aa
FIGURE 1A htt Q23
~90 aa
htt Q41
~110 aa
htt Q67
~135 aa
FIGURE 2A

```
                          SEQUENCE LISTING

<160> NUMBER OF SEQ ID NOS: 4

<210> SEQ ID NO 1
<211> LENGTH: 19
<212> TYPE: PRT
<213> ORGANISM: Artificial Sequence
<220> FEATURE:
<223> OTHER INFORMATION: synthetic

<400> SEQUENCE: 1

Asp Asp Gln Gln Gln Gln Gln Gln Gln Gln Gln Gln Gln Gln Gln
1               5                   10                  15

Gln Lys Lys

<210> SEQ ID NO 2
<211> LENGTH: 28
<212> TYPE: PRT
<213> ORGANISM: Artificial Sequence
<220> FEATURE:
<223> OTHER INFORMATION: synthetic

<400> SEQUENCE: 2

Arg Arg Arg Arg Arg Gln Gln Gln Gln Gln Gln Gln Gln Gln Gln
1               5                   10                  15

Gln Gln Gln Gln Gln Gln Gln Arg Arg Arg Arg Arg
                20                  25

<210> SEQ ID NO 3
<211> LENGTH: 36
<212> TYPE: DNA
<213> ORGANISM: Artificial Sequence
```

```
<220> FEATURE:
<223> OTHER INFORMATION: synthetic

<400> SEQUENCE: 3
gaattcgcca tggcgaccct ggaaaagctg atgaag                    36

<210> SEQ ID NO 4
<211> LENGTH: 39
<212> TYPE: DNA
<213> ORGANISM: Artificial Sequence
<220> FEATURE:
<223> OTHER INFORMATION: synthetic

<400> SEQUENCE: 4
tctagactat tcggtgcagc ccggctcctc agccacagc                 39
```

US 6,794,414 B1

METHOD AND COMPOSITIONS FOR TREATING DISEASES MEDIATED BY TRANSGLUTAMINASE ACTIVITY

The present application is the national stage under 35 U.S.C. 371 of PCT/US99/13615, filed Jun. 17, 1999 which claims the benefit of U.S. Provisional Application No. 60/089,603, filed Jun. 17, 1998.

FIELD OF INVENTION

The present invention is directed to methods and compositions for treating diseases mediated by transglutaminase activity, by inhibiting the activity of transglutaminase.

BACKGROUND OF THE INVENTION

Protein cross-linking resulting in the formation of aggregates is a common feature of a number of neurodegenerative diseases, including Alzheimer's disease and the family of diseases exemplified by Huntington's Disease, caused by expansion of CAG trinucleotides encoding polyglutamine (Green, 1993; Prosiner et al, 1983; Davies et al, 1997; Scherzinger et al, 1997; DiFiglia et al, 1997).

Several neurodegenerative diseases, including Huntington's Disease, spinobulbar atrophy (Kennedy's disease), various spinocerebellar ataxias (SCA 1, 2, 3, 6, 7), and dentatorubralpallidoluysian atrophy (DRPLA), involve proteins with long stretches of polyglutamines in their N-terminus (Ross, 1995). Cross-linking of these polyglutamine containing proteins may be critical in the neurologic dysfunction and pathology characteristic of these disorders (Ross, 1995). Recently, nuclear inclusions containing ubiquinated aggregates of huntingtin (htt), DRPLA protein, ataxin 1 and ataxin 3, respectively, have been observed in the affected brain areas of patients with Huntington's Disease, DRPLA, SCA-1 and SCA-3 (DiFiglia et al, 1997; Igarashi et al, 1998; Skinner et al, 1997; Paulson et al, 1997). Interestingly, both htt and ataxin 3 are primarily cytoplasmic proteins in healthy individuals.

In Huntington's Disease, as well as in spinobulbar atrophy, various spinocerebellar ataxias (SCA 1, 2, 3, 6, 7) and dentatorubralpallidoluysian atrophy, the gene encoding the mutant protein contains expanding trinucleotide repeats of the codon CAG. These repeats encode glutamine (Q). With each ensuing generation, because of the expansion of these repeats, disease onset is earlier, a phenomenon known as genetic anticipation. There is no genetic anticipation, however, when the disease is transmitted through the female line in Huntington's Disease. The importance of the polyglutamine domain is further emphasized by the observation that CAG repeats, ectopically introduced into an unrelated gene encoding hypoxanthine phosphoribosyltransferase (hrpt), produce a phenotype similar to that seen in the human neurologic disorders related to abnormal polyglutamine domains (Ordway et al, 1997). The length of the polyglutamine domain is absolutely critical for the appearance of Huntington's Disease, as well as the other neurologic diseases involving mutations in genes involving expansion of CAG repeats. In Huntington's disease, for example, if the polyglutamine domain exceeds 36 Q repeats, the fatal neurologic disease ensues. In other CAG trinucleotide repeat diseases, there is a pathologic threshold, although the length varies from disease to disease, with the shortest threshold (21Q) in SCA-6, and longer thresholds in SCA-3 (61Q) and dentatorubralpallidoluysian atrophy (49Q) (Lunkes et al, 1997).

Huntingtin is expressed at similar levels in patients with Huntington's Disease and controls, regardless of the number of glutamine repeats. Huntingtin is also expressed throughout all tissues of the body and is expressed in equal amounts in all regions of the normal brain. In affected areas of Huntington's disease brain, mutant huntingtin is much less abundant than wild-type huntingtin (Schilling et al, 1995; Trottier et al, 1995; Strong et al, 1993). Although the Huntington's Disease gene is widely expressed (Huntington's Disease Collaborative Research Group, 1993; Sharp et al, 1995), the pathology of Huntington's Disease is restricted to the brain, and to specific regions within the brain, for reasons that remain poorly understood. At death the brain is small and often weighs less than one kilogram, as compared to the brain of a normal young adult, which weighs 1.4 kg. The frontal and parietal lobes are smaller than normal, but the most distinctive damage is visible in the head of the caudate nucleus, which is shrunken, along with the putamen and globus pallidus. The pathologic signature of Huntington's Disease is the loss of virtually all medium spiny neurons in the caudate. The brainstem and cerebellum are normal. Microscopically, there is extensive loss of neurons in the caudate and putamen, with evidence for apoptosis and necrosis (Portera-Caillau et al, 1995).

Huntingtin is located in neurons throughout the brain, with the highest levels evident in larger neurons. Huntingtin is a cytosolic protein primarily found in somatodendritic regions (Sharp et al. 1995; Strong et al, 1993). Recently, immunocytochemrical studies, using antibodies generated against peptides corresponding to the huntingtin N-terminus, suggest that inclusions containing huntingtin are present in the nucleus of striatal neurons of Huntington's Disease patients, but not in their cerebellar or brainstem neurons (DeFiglia et al, 1997). In the adult form of Huntington's Disease, axonal inclusions in dystrophic neurites are far more common than nuclear inclusions (DiFiglia et al, 1997). These inclusions are never found in normal individuals. These inclusions contain aggregates of huntingtin. These inclusions do not have the appearance of amyloid: "searches for amyloid deposits in brains of Huntington's Disease patients have been negative." (Lunkes et al, 1997).

These aggregates stain with antibodies directed to the N-terminus of huntingtin but not to the C-terminus. The huntingtin N-terminal fragment, containing the polyglutamine domain, is most likely bound to ubiquitin via a lysine ubiquitin bond (Ciechanover, 1994). Somehow, in the pathogenesis of Huntington's Disease, the mutant huntingtin translocates to the nucleus and forms inclusions composed of aggregated N-terminal fragments of huntingtin. This is a pathological feature of the disease (Davies et al, 1997; Scherzinger et al, 1997; DiFiglia et al, 1997). Recently ubiquitinated intranuclear inclusions containing expanded polyglutamine domains were also seen in neurons in dentatorubralpallidoluysian atrophy (Igarashi et al, 1998), spinocerebellar ataxia type 3 (Paulson et al, 1997) and in spinocerebellar ataxia type 1 (Skinner et al, 1997).

Two mechanisms have been postulated to explain the cross-linking of huntingtin; these mechanisms may not be mutually exclusive. Molecular modeling had shown that β-strands made of polyL-glutamine can be assembled into sheets or barrels by hydrogen bonds between their main-chain and side-chain amides (Perutz et al, 1994). Perutz and colleagues (Stott et al, 1995; Perutz, 1996) tested this model experimentally. They showed that synthetic polyL-glutamine (Asp2-Q15-Lys2) (SEQ ID NO:1) forms β-strands, which are held together by hydrogen bonds between their amide groups. These aggregates maintain their secondary structure at pH 7 and pH 3. Interestingly, at pH 7 the peptide gradually precipitated. They postulated that these polymers comprised of polar zippers may be responsible for the neurodegeneration seen in Huntington's Disease. Recently, Scherzinger and colleagues showed that a glutathione S-transferase (GST) fusion protein encoding part of exon 1 of huntingtin, containing a polyglutamine domain of 51Q, spontaneously aggregates into amyloid-like fibrils, after enzymatic cleavage of the GST protein together with a few amino acids of exon 1 of huntingtin (Scherzinger et al, 1997) The GST-huntingtin Q51 construct was soluble; aggregates were formed only upon total enzymatic cleavage of the GST tag from GST-httQ51. Somehow, covalent fusion of the peptide with the polyglutamine domain to an unrelated protein, GST, prevented aggregation.

The GST-htt intermediate may serve as a nucleation factor for ordered protein aggregation in this system (Scherzinger et al, 1997). Indeed, this model is supported by the experimental finding of intermediate structures, termed "clots", on one or both ends of the growing fibrils. Scherzinger and colleagues stated, "These clots were not detected when GST-httQ51 was digested to completion with trypsin, which totally degrades the GST tag, while they were detectable upon limited digestion, leaving the GST moiety intact. This indicates that these structures are transient intermediates." Expression of a GST-htt fusion protein may, thus, have allowed the GST to act as an intermediate, allowing for the aggregation of htt.

Green (1993) proposed a second hypothesis to explain huntingtin aggregation. Green suggested that polyglutamine tracts above a certain pathologic length become better substrates for transglutaminase. The resulting aggregated huntingtin, either cross-linked within itself or with other proteins, then becomes toxic for neurons.

Transglutaminases are a family of $ca^{2+}$ dependent enzymes that catalyze the formation of isopeptide bonds between the side chains of glutamine and lysine (K) residues. When a protein-bound K residue serves as the primary amine donor, the reaction results in the formation of an $\epsilon$-($\gamma$-glutamyl)-Lys isopeptide bond that serves to cross-link the proteins (Green et al, 1993; Folk, 1980). In addition to proteins containing lysine, the polyamines spermidine and spermine may serve as substrates for transglutaminases. The resulting bond is covalent, stable and relatively resistant to proteolysis (Folk, 1980). This cross-linking occurs between two glutamine residues (in the presence of a diamine) or between one glutamine residue and a K residue. When such a bridge is formed between two glutamine residues, it is possible that an adaptor molecule provides the diamine donor which is involved. It is postulated that transglutaminases promote cross-linking between various domains within the Huntington's Disease protein and other cellular proteins.

Little is known about how huntingtin interacts with itself or with other proteins. Kahlem et al showed that polyglutamine peptides, when flanked by adjacent amino acids from the residues found in the proteins associated with SCA-1, SCA-3, and dentatorubralpallidoluysian atrophy (DRPLA), or flanked by arginine, could serve as a substrate for arginine transglutaminase (RTGase) (Kahlem et al, 1996). Peptides with Q>18 could not be used in those studies, because of their instability and their tendency to form spontaneous aggregates. In the presence of a brain extract from rat containing transglutaminase activity and $R_5Q_{18}R_5$ (SEQ ID.NO:2), as glutamine acceptor, and a rat brain protein fraction as amine donor, brain proteins were aggregated due to the endogenous transglutaminase activity in the extract (Kahlem et al, 1996).

Although they did not work with GST constructs of huntingtin, Cooper et al showed that either GST-Q10 or GST-Q62 could serve as substrates for tissue transglutaminase (Cooper et al; 1997). Previously, they had shown that huntingtin and the DRPLA protein bind selectively to glyceraldehyde 3-phosphate dehydrogenase (GAPDH) in brain homogenates (Burke et al, 1996). GAPDH in brain homogenates bound to an immobilized Q60 polypeptide, but not to an immobilized Q20 peptide. Moreover, transglutaminase could inhibit GAPDH to a greater extent in the presence of GST-Q62 or GST-Q81 than in the presence of GST-10. These experiments imply that polyglutamine domains disrupt cerebral energy metabolism after aggregation with transglutaminase.

Insulin-dependent diabetes mellitus (IDDM) in NOD mice and mouse experimental autoimmune encephalomyelitis (EAE) are the major disease models for human type I diabetes and multiple sclerosis, respectively. Compared with the Interleukin-2 (IL-2) protein produced by B6 mice, NOD-produced IL-2 shows differences in glycosylation that may affect its functional half-life. If the NOD/SJL allele of IL-2 influences EAE and diabetes susceptibility, a possible mechanism may lie in its role in T-cell selection in the thymus or in its function in the peripheral immune compartment. Insufficient levels of IL-2 may affect negative selection in the thymus, allowing the escape of self-reactive T-cells. IL-2 is also important in the autocrine feedback loop that regulates the expansion of antigen-specific T-cell clones by inducing apoptotic cell death, and is essential for the maintenance of self-tolerance as evidenced by the development of severe autoimmunity in IL-2 mice (Encinas et al., 1999).

SUMMARY OF THE INVENTION

It is an object of the present invention to overcome the aforesaid deficiencies in the prior art.

It is another object of the present invention to inhibit in vivo the activity of transglutaminase.

It is a further object of the present invention to treat neurological diseases involving aggregation of polyQ proteins, such as huntingtin.

It is another object of the present invention to treat neurological diseases presenting aggregated polyQ proteins by inhibiting the activity of transglutaminase.

It is a further object of the present invention to treat diseases mediated at least in part by transglutaminase by administering an inhibitor for transglutaminase.

It is another object of the present invention to treat cell-mediated autoimmune diseases by administering an inhibitor of transglutaminase.

It is a further object of the present invention to treat diseases characterized by inflammatory infiltrates in the central nervous system by inhibiting the activity of transglutaminase.

It is another object of the present invention to treat multiple sclerosis by inhibiting the activity of transglutaminase.

Neurodegenerative diseases involving cross-linking of polyQ proteins, resulting in the formation of aggregates, can be treated by inhibiting the action of transglutaminase. Treatment includes reversing ongoing paralysis as well as lymphocytic infiltration in the brain. This inhibition can be effected by administering to a patient in need thereof an effective amount of a compound which inhibits the activity of transglutaminase, thereby inhibiting or reversing cross-linking of the polyQ proteins. Compounds which have been found to inhibit transglutaminase activity include monodansyl cadaverine, monoamines and diamines such as cystamine, putrescine, GABA (gamma-amino benzoic acid), N-benzyloxy carbonyl, 5-deazo-4-oxonorvaline p-nitrophenylester, glycine methyl ester, $CuSO_4$, and the oral anti-hyperglycemic agent tolbutamide.

The activity of transglutaminase can also be inhibited by means of gene therapy. By this means, a DNA sequence which inhibits or prevents the activity of transglutaminase, or which encodes a polypeptide which inhibits or prevents the activity of transglutaminase, can be delivered directly to the cells of interest. Such a substance may be a DNA or RNA sequence which is antisense to the transglutaminase gene, thereby preventing its transcription and expression. Alternatively, the DNA delivered to the cells of interest may encode a polypeptide which is an inhibitor of transglutaminase or which otherwise prevents the activity of transglutaminase. Such a polypeptide may be an antibody, including a single chain antibody or the antigen binding domain of an antibody, which will bind to transglutaminase and thereby inhibit its activity. A short peptide which is a substrate for transglutaminase and therefore prevents its action on the polyQ protein may also be used. Such a peptide can readily be designed by one of ordinary skill in the art.

Additionally, because interleukin-2 is a polyQ molecule, cell-mediated autoimmune diseases can be created by inhibiting transglutaminase activity by any of the methods disclosed herein and thus inhibiting crosslinking of interleukin-2. Such diseases include multiple sclerosis, rheumatoid arthritis, and insulin dependent diabetes mellitus.

Because transglutaminase is critical for adherence of activated lymphocytes to inflamed brain endothelium and for the subsequent passage of lymphocytes into the central nervous system, inflammatory diseases of the central nervous system can be treated by inhibiting transglutaminase activity by any of the means disclosed herein.

BRIEF DESCRIPTION OF THE DRAWINGS

FIG. 1A illustrates constructs used in translation showing the location and size of polyglutamine repeats.

FIG. 2A illustrates constructs used in translation showing the location and size of polyglutamine repeats.

DETAILED DESCRIPTION OF THE INVENTION

Figure 1B:
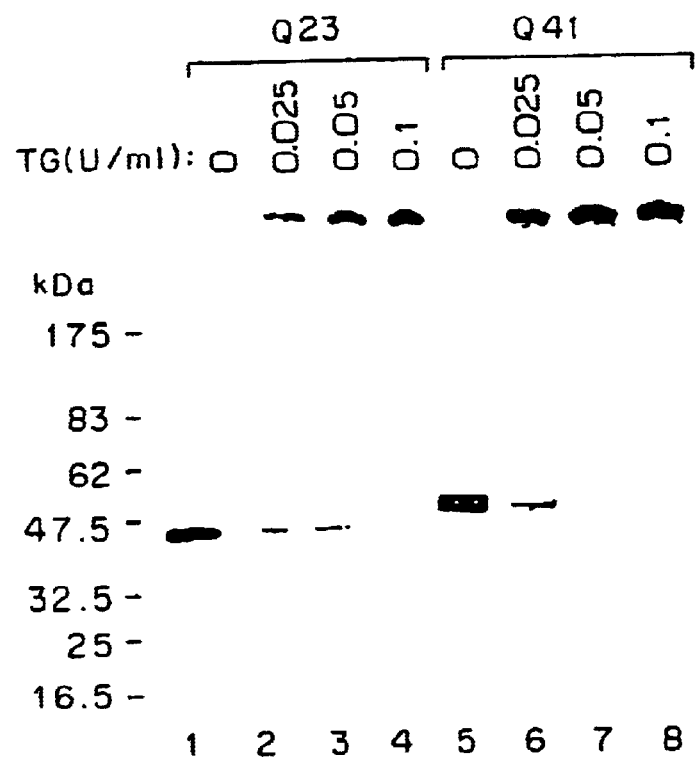
FIG. 1B shows in vitro expression of httQ23 and httQ41.

A number of neuradegenerative disorders, including Huntington's Disease, linked spinal and bulbar muscular atrophy, spinocerebellar ataxia type 1, dentatorubralpallidoluysian atrophy, and Machado-Joseph disease, are caused by dynamic mutations in which CAG repeats encoding polyglutamine domains in specific proteins are directly associated with the disease. Transglutaminase is involved in cross-linking these proteins, such as ataxin in spinocerebellar ataxia, or huntingtin in Huntington's Disease, with other proteins, e.g., ubiguitin, resulting in their eventual metabolism and degradation within neurons. Transglutaminases catalyze the formation of $\epsilon$-($\gamma$-glutamyl)-lysine between protein molecules. These cross-linked molecules are degraded with a residual isodipeptide $\gamma$-glutamyl lysine remaining. Increasing the length of the polyglutamine tract inhibits transglutaminase activity.

Aggregated huntingtin in the nuclei of neurons and in dystrophic neurites in the brain are pathologic hallmarks of Huntington's Disease (DiFiglia et al, 1997). Nuclear inclusions are also found in mice transgenic for the HD mutation; these inclusions have many of the neurologic features of patients with Huntington's Disease (Davies et al, 1997).

A variety of proteins have been shown to interact with huntingtin. Two of these proteins, GAPDH (Burke et al, 1996) and HAO-1 (Li et al, 1995), have an enhanced association with huntingtin with increasing length of the Q domain. No further evidence is available about whether these brain associated proteins could be nucleation factors that participate in the aggregation of huntingtin with Q>36. The exact chemical details of the physical interactions of the proteins with huntingtin remains unsolved.

While it is not a proven mechanism for aggregation, it has been proposed that spontaneous aggregation is involved. One hypothesis is that the physical properties of polyglutamine domains organize themselves into polar zippers from $\beta$-strands that can be assembled into sheets or barrels by hydrogen bonds formed between their main-chain and side-chain amides (Perutz et al, 1994). However, it has been found that synthetic polyglutamine polymers containing polyQ domains far shorter than the pathological threshold of Q36 in Huntington's Disease, spontaneously aggregate in an aqueous medium. A variation of this hypothesis has been described by Scherzinger and colleagues (Scherzinger et al, 1997) who showed that huntingtin, with glutamine above the threshold of 36, aggregates after proteolytic cleavage of the glutathione S-transferase (GST) domain. Before GST cleavage, GST-httQ51 is soluble, while aggregates do form with GST-htt fragments containing Q83 or Q122. During the process of aggregation, knobs were observed on the nascent amyloid like fibrils, and the knobs are likely to be GST. Glutathione S-transferase, thus, is believed to act as a nucleation factor in the formation of the amyloid (Jarrett et al, 1993). It is possible that GST is an artifact of the molecular biological technique of protein expression in bacteria, and GST plays no pathophysiological role in Huntington's Disease.

There are essential differences between amyloid aggregates and the aggregates cross-linked with transglutaminase. These aggregates cross-linked with transglutaminase have been reported in neuronal nuclear inclusions in affected cases of Huntington's Disease brain, particularly those of juvenile onset, and in intranuclear inclusions in the dentate in DRPLA. Aggregates have also been reported in intranuclear inclusions in affected areas of brain in a juvenile patient with SCA-1 (Skinner et al, 1997) and in intranuclear inclusion in neurons of affected areas of MJD brain (Paulson et al, 1997).

Kahlem et al. studied guinea pig transglutaminase (TGase) and TGase isolated from rat brain (Kahlem et al., 1998). They showed that htt isolated from the brains of juvenile Huntington's Disease patients could be crosslinked in vitro into aggregates. To date, no one has reported on the activity of TGase in the Huntington's Disease brain, on the biophysical properties of the aggregates catalyzed by TGase, or on the optical properties of inclusions in the Huntington's disease brain.

Aggregates Cross-Linked with Transglutaminase are not Amyloid

The aggregates formed in vitro after cleavage of the GST-tag, reported by Scherzinger and colleagues, have the properties of amyloid, staining with Congo Red dye, and showing green birefringence under polarized light (scherzinger et al, 1997). However, no amyloid inclusions have been reported in Huntington's Disease brain (Lunkes et al, 1997). The appearance of aggregates under electron microscopy does not have the appearance of amyloid (DiFiglia et al, 1997). The aggregate bodies in DRPLA, another polyglutamine disease, do not stain with Congo Red (Igarashi et al, 1998). The aggregates of huntingtin cross-linked with transglutaminase stain only weakly with Congo Red, but do not show green birefringence, and cannot be considered amyloid (Robbins, 1967).

Huntinatin is Soluble

Full-length huntingtin, including huntingtin with polyglutamine expansions in the pathologic range, does not spontaneously aggregate in vitro (Persichetti et al, 1995; Kahlem et al, 1998). Short in vitro translated fragments of 90 to 330 amino acids from the N-terminus of huntingtin, as well as longer in vitro translated portions of the N-terminal portion of huntingtin of length 50–60 kD containing Q91, do not aggregate in vitro. Aggregates are not seen in most cells in Huntington's Disease, even though the mutant huntingtin is ubiquitously expressed.

It is not certain if concentration differences can be used to reconcile the opposing data and conclusions. It is possible that aggregation is not seen with in vitro translated httQ41 or httQ67, or the larger 50–60 kD fragment of httQ91 reported by Goldberg (Goldberg et al, 1996) as the concentration of the translated protein is not high enough to start the aggregation process. It is known that for the formation of fibrillar aggregates a concentration of about 30–100 mM is required. Whether the concentration used in the in vitro translation studies, or the concentration used in the system employing a bacterial fusion protein, is a better reflection of the in vivo milieu in the cell cannot be answered. However, the fusion tag, GST, covalently linked to a portion of the huntingtin, does not accurately reflect the condition of huntingtin in vivo.

Since httQ41 and httQ67 failed to spontaneously aggregate, it was believed that transglutaminase catalyzed cross-linking might explain the formation of nuclear inclusions in Huntington's Disease. Experiments were conducted to define the role of transglutaminase in brain material from Huntington's Disease patients and in mice transgenic for the Huntington's Disease mutation. The following pieces of experimental evidence were obtained which support the role of transglutaminase in the pathogenesis of Huntington's disease:

(1) Transglutaminase can creoss-link httQ23, httQ41, and httQ67.

(2) More aggregation occurs in httQ41 (110 amino acids) and Q67 (135 amino acids) than in httQ23 (90 amino acids). There was seen no dependence on the length of the polyQ domain and the amount of transglutaminase catalyzed aggregation with a larger fragment httQ23 (310 amino acids) versus httQ41 (330 amino acids). More aggregation catalyzed by transglutaminase is seen with polyQ proteins than with luciferase, a protein without a polyQ domain.

(3) There is transglutaminase activity in Huntington's Disease brain, and it is increased compared to control brain. The transglutaminase activity is increased in the nuclear fraction of Huntington's Disease brain compared to the nuclear fraction from control brain.

(4) In mice transgenic for the Huntington's Disease mutation, transglutaminase activity is also increased.

(5) Transglutaminase is found in both the cytoplasm and in the nuclei of Huntington's Disease brain.

(6) Transglutaminase itself appears to be associated with aggregates formed in vitro.

The above observations suggest that transglutaminase-catalyzed cross-linking of huntingtin plays a role in the formation of aggregates in the nucleus of Huntington's Disease brain.

It was found that transglutaminase can cross-link itself and anti-transglutaminase antibody stains the $^{35}$S aggregates of httQ23 and httQ41. A covalent association between transglutaminase and substrate in the pathogenesis of a disease has precedent in celiac disease, wherein IgA antibodies are directed to transglutaminase. In this inflammatory disease of the gastrointestinal system, the enzyme transglutaminase and its substrate, the glutamine high protein, gluten, may form a neoantigen, which then serves as the target for autoimmune attack (Steinman, 1995; Dietrich et al, 1997).

Evidence for the role of transglutaminase in the formation of nuclear inclusions is reinforced by the observation that transglutaminase activity is increased in nuclei isolated from brain relative to cytoplasm. Huntingtin is normally found in the cytoplasm. It is hypothesized that the ubiquitinated huntingtin in Huntington's Disease translocates to the nucleus, instead of entering the cytoplasmic proteasome. Huntingtin is trapped in the nucleus because it interacts with a nucleus-specific carrier. For example, huntingtin interacts with a nuclear protein, perhaps a protein like leucine-rich acidic nuclear protein which has been shown to interact with ataxin-1, another polyglutamine protein which causes neurologic disease (Skinner et al, 1997; Matilla et al, 1997). The interaction with such a nuclear protein might be stronger with longer glutamine domains in the huntingtin, similar to what is seen with ataxin 1 in SCA-1 (Skinner et al, 1997; Matilla et al, 1997).

Once in the nucleus, nuclear transglutaminase causes the cross-linking of huntingtin-ubiquitin complexes, and this is toxic for neurons because the cross-linked untingtin-ubiquitin complexes cannot be processed by uclear proteasomes. Interestingly, the huntingtin-ubiquitin linkage leaves the glutamine intact, since the huntingtin-ubiquitin bond is likely via the ε-amino group on lysine (Ciechanover, 1994; Ciechanover et al, 1998).

Cytoplasmic, as well as nuclear transglutaminase activity, is also increased in Huntington's Disease brain. it is intriguing that in lymphoblastoid lines, it has been shown that transglutaminase activity is decreased in lymphoid cells from Huntington's Disease patients compared to controls (Cariello et al, 1996). It is as yet unsolved why the observation of increased transglutaminase activity is brain specific. This may help explain why the pathology of Huntington's Disease is restricted to the brain, while huntingtin is widely expressed outside the brain. It should be noted that with any theory involving spontaneous aggregation of huntingtin with Q>36, it would be difficult to explain the regional specificity of the trinucleotide repeat diseases. Huntingtin is ubiquitously expressed throughout the body, yet disease is present in only certain regions of the brain. In contrast, if various transglutaminases are under different regulatory controls in different anatomic compartments, region specificity might one day be explained.

It has been discovered that transglutaminase activity is increased in Huntington's Disease, and more aggregation is seen with increasing length of polyQ in huntingtin. Using transglutaminase from rat brain extracts, Green and colleagues recently showed that huntingtin is a substrate of transglutaminase in vitro and that the rate constant of the reaction increases with length of the polyQ over a range of an order of magnitude (Kahlem et al, 1998). Of course, Green never measured transglutaminase activity in Huntington's Disease, but only used human lymphoblastoid transglutaminase and rat brain transglutaminase. Because Cariello et al (1996) and the present inventors demonstrated that transglutaminase activity is actually decreased in human lymphoblastoid lines, one skilled in the art would expect that the normal rat brain would be a poor indicator of diseased human brain. Indeed, the present inventors found increased levels of activity of endogenous transglutaminase in Huntington's Disease brain, but not in lymphoblastoid cells. Increased transglutaminase activity was also seen in the brains of mice transgenic for the huntingtin mutation.

Green found that huntingtin is a substrate of lymphoblastoid transglutaminase and rat brain transglutaminase. However, given the finding that transglutaminase activity is actually decreased in human lymphoblastoid lines, it is absolutely unpredictable that inhibiting transglutaminase activity could treat neurodegenerative diseases presenting aggregated proteins such as in Huntington's Disease. From the lymphoblastoid results Green obtained, one would want to enhance rather than inhibit transglutaminase activity.

TGase Assay on Huntington's Disease Brains and Lymohoblastoid Cells

Each assay contained 80 µg of brain extract, 4 mg/ml N,N-dimethylated casein, 50 mM Tris (pH 8.0), 5 mM $CaCl_2$, 5 mM dithiothreitol (DTT), and 0.37 mM putrescine (1:5, $^3$[H]putrescine:putrescine) in 80 µL. The reaction was incubated at 37° C. for 30 minutes. After it was washed in 500 µL of 10% trichloro acetic acid (TCA) and washed again in 100% ethanol, the reaction was resuspended in 220 µL of 0.1 M NaOH. The resuspended pellet was added to 10 ml of scintillation liquid. Specificity was demonstrated with 5 mM mono dansyl cadaverine. For lymphoid cells, $10^6$ cells were suspended in 0.5 ml buffer for five minutes, then centrifuged at 1200×g for ten minutes.

Extracts from Human Brains

Tissues were obtained from the Baltimore Huntington's Disease Project Brain Bank, Johns Hopkins School of Medicine. The Huntington's Disease material was from a 32 year old patient with a Vonsattel scale of 4 and htt of Q60/Q19 (the number of Q residues divided by each allele of the htt gene); a 43 year old patient with a Vonsattel scale of 4 and htt of Q56/Q19 a 38 year old patient with a Vonsattel scale of 3 and htt of Q63/Q26; a 43 year old patient with htt of Q53/Q20; and a 75 year old patient with htt of Q44/Q16. Control brains came from 30 to 80 year old patients. Postmortem examinations were performed within thirteen hours.

Approximately 500 mg of brain tissue was homogenized in 2 ml of 10 mM Hepes (pH 7.4) containing 150 mM NaCl, 0.2 mg/ml leupeptin, 0.2 mg/ml aprotinin, 0.2 mg/ml pepstatin, and 0.5 mM phenylmethylsulfonyl fluoride (PMSF). The homogenate was centrifuged at 4° C. for ten minutes at 1000×g, and the supernatant was then centrifuged at 4° C. for ten minutes at 10,000×g to separate the cytoplasmic proteins. The remaining nuclear pellet was washed twice, for ten minutes each time, with the homogenization buffer at 4° C. at 1000×g, and then suspended in 1 ml of 10 mM Tris-Cl, 140 mM NaCl, 3 mM $MgCl_2$, 0.5 mM PMSF, 0.1% sodium dodecyl sulfate (SDS), and 1% Nonylphenyl-polyethylene glycol (Nonidet P-40) (pH 7.4). The homogenate was spun at 4° C. for ten minutes at 8000×g. This procedure increased the level of beta-demn, a protein found more frequently in the cytoplasm than in the nucleus, enriching it 15.5-fold in the cytoplasm relative to the nucleus (Zhao et al, 1998).

Electrophoresis and Western Blot Analysis

One hundred µg of protein was loaded onto 10% polyacrylamide/SDS gels. After electrophoresis, the proteins were transferred to nitrocellulose membranes and detected using the enhanced chemiluminescence system (Amersham). Affinity-purified anti-TGase antibody was used at 1:1250.

Affinity-Purified Antibodies Against TGase

TGase C (300 µg, Sigma) was diluted in 500 µL of phosphate buffered saline (PBS) and suspended in 500 µL of complete Freund's adjuvant for the first two injections. For the third injection, the TGase in PBS was suspended in 500 µL of incomplete Freund's adjuvant. Each rabbit was injected each time with a total of 300 µg of protein. The first two injections were given with an interval of three weeks, and the third injection was given one month after the second. Antisera were passed over an affinity column of AffiGel (crosslinked agarose affinity support for coupled protein) (Bio-Rad) coupled with TGase C.

htt DNA Constructs and in vitro Translation cDNA constructs containing 330 amino acids of the N terminus of htt with 23 or 44 glutamine repeats were a gift of Christopher Ross. These were subcloned directionally as BamHI/NotI fragments into the vector pcDNA3(+) under the control of the T7 promoter (Invitrogen).

An htt cDNA construct containing approximately the first 135 amino acids of the N terminus with 67 glutamines and a large 5'-untranslated region was a gift of Richard Myers. A construct lacking the 5'-untranslated region was made by performing PCR using the construct as a template and the primer pair 5'-GAATTCGCCATGGCGACCCTGG AAAAGCTGATGAAG-3' (SEQ ID NO:3) and 5'-TCTAGACTATTCGGTGCAGCCCGGCTCCTCAG CCACAGC-3' (SEQ ID NO:4). The PCR product was cloned into pTasgeT under control of the the T7 promoter (Promega). The same PCR primer pair was also used on the previously mentioned Q23 and Q41 constructs.

For incubation with TGase, 5 µL of each of these products was incubated for 45 minutes at 37° C. in a 20 µL volume containing the following: 50 mM Tris (pH 8.0), 5 mM $CaCl_2$, 5 mM DTT, and appropriate concentration of guinea pig liver TGase (Sigma). Inhibition of the TGase-mediated aggregation was demonstrated by co-incubation with a monoclonal antibody, CUB7402 (NeoMarkers, Union City, Colo.) at 80 micrograms/ml. For Western analysis, another monoclonal antibody against TGase, TG100 (NeoMarkers) was used at 1:2000.

Congo Red Staining of Human Huntington's Disease Tissue and Identification of Inclusions The neocortex of a juvenile Huntington's Disease patient from the Baltimore Huntington's Disease Project Brain Bank and an elderly male with Alzheimer's disease from the University of New Mexico Brain Bank were studied. Sections were deparaffinized, stained with Congo red and hematoxylin counterstain, and photographed. Identical sections were then subjected to a polyclonal antibody to ubiquitin (DAKO, Carpinteria, Calif.). Sections were treated with hydrogen peroxide/methanol, microwaved for several minutes, blocked with 3% normal goat serum, incubated with primary antibody at room temperature overnight for 16–20 hours, and developed using avidin-biotin complex reagents (vector Laboratories), 3,3'-diaminobenzidine chromagen, and a brief hematoxylin counterstain.

Diseases involving transglutaminase-mediated aggregate formation can be successfully treated by inhibiting transglutaminase activity. Thus, neurodegenerative disorders presenting aggregated polyQ proteins, such as Huntington's Disease, linked spinal and bulbar muscular atrophy, spinocerebellar ataxia type 1, dentatorubral-pallidoluysian atrophy, and Machado-Joseph disease, can be treated by administering to a patient affected with such a neurodegenerative disorder a compound that inhibits transglutaminase activity, such as monodansyl cadaverine or tolbutamide. Paraparetic experimental animals treated in vivo with monodansyl cadaverine were free of disease after treatment with no untoward side effects.

Inflammatory Diseases of the Central Nervous System and Cell-Mediated Autoimmune Diseases It has been discovered that administration of a transglutaminase inhibitor, such as monodensyl cadaverine, can reverse ongoing paralysis in paraparetic mice with experimental autoimmune encephalomyelitis. The mechanism of this action is not yet fully understood. It is possible that such activity is related to the activity relating to neurodegenerative diseases presenting aggregated polyQ proteins, discussed above. Susceptibility of mice to the experimental models of IDDM and MS has been mapped to a polymorphism in the IL-2 gene (Encinas et al, 1999). IL-2 is a polyQ molecule, as are the molecules involved in aggregation in the neurodegenerative diseases. IL-2 is important in the prevention of autoimmune diseases. Insufficient levels of IL-2 may affect negative selection in the thymus, allowing the escape of self-reactive T cells. If the polyQ region of IL-2 becomes unusually long, transglutaminase may cause crosslinking. of the polyQ regions, thus blocking the effectiveness of IL-2. Such a mechanism would affect the course of all cell mediated autoimmune diseases, such as IDDM, multiple sclerosis, rheumatoid arthritis, and others.

Another possible mechanism for the effect observed in the treatment of EAE with transglutaminase inhibitor may relate to the critical role of transglutaminase in the adherence of activated lymphocytes to inflamed brain endothelium and for the subsequent passage of lymphocytes into the central nervous system. Administration of a transglutaminase inhibitor reduced paralytic disease in an animal model of multiple sclerosis, experimental autoimmune encephalomyelitis (EAE), and prevented the accumulation of inflammatory lymphocytes in the brain. If the effect of transglutaminase inhibitor is caused by this mechanism, it would be expected that administration of transglutaminase inhibitor will be effective in reducing inflammation in any inflammatory disease of the central nervous system, such as, but not limited to, multiple sclerosis.

Experimental

Experiments were conducted to determine whether transglutaminase could cross-link polyglutamine domains on huntingtin proteins which contain polyglutamine of various lengths. Further experiments were conducted to examine the activity of transglutaminase in Huntington's Disease and control brains. It was found that spontaneous cross-linking of huntingtin with polyglucamine domains greater than 36 does not occur. Instead, transglutaminase catalyzed cross-linking plays the critical role in the pathogenesis of neurodegenerative diseases characterized by transglutaminase cross-linking of polyQ proteins.

Transclutaminase Cross-Links a Fragment of Translated htt Containing the PolyQ Domain To determine whether soluble huntingtin constructs could be cross-linked by transglutaminase in vitro, a rabbit reticulocyte lysate system was used to translate transcripts containing portions of exon 1 of huntingtin with polyQ23, polyQ41, or polyQ67. A 310 amino acid fragment was constructed, beginning with the N-terminal methionine of huntingtin, corresponding to a predicted 50 kDa protein. This length was chosen because a 50 kDa band in total protein homogenates and in nuclear extracts is detected in Huntington's Disease cortex but not in control brain (DiFiglia et al, 1997). This fragment stains with an antibody against the N-terminus of huntingtin. Smaller immunoreactive bands are also seen, which may be degraded products of the 40 kDa fragment, or different sites of cleavage. Thus, httQ23 is a 310 amino acid fragment of the N-terminus of huntingtin, and httQ41 is a 330 amino acid fragment, as shown in FIG. 1A. A 90 amino acid fragment was constructed from the N-terminus of httQ23, a 100 amino acid fragment from httQ41, and a 135 amino acid fragment, httQ67, as shown in FIG. 2A.

In FIG. 1A, each construct is drawn approximately to scale and the size of the amino acid regions is shown. Each construct begins with the amino terminal methionine of the htt protein. The dark bar indicates the location and size of the polyglutamine repeats.

The httQ23, httQ41, and httQ67 were intrinsically labelled with $^{35}S$ methionine. FIG. 1B shows that upon addition of transglutaminase, both httQ23 (310 amino acids) and httQ41 (330 amino acids) aggregate into a high molecular weight polymer within 30 minutes. There was no increase in the amount of aggregation with the longer httQ41 as compared to the httQ23, cf. FIG. 1C. FIG. 2B shows similarly that, upon addition of transglutaminase, httQ23 (90 amino acids), httQ41 (100 amino acids), and httQ67 (135 amino acids) all aggregate into a high molecular weight polymer within 30 minutes. In FIG. 2C, it can be seen that there is an increased amount of aggregation with the constructs httQ41 (110 amino acids) and httQ67 (135 amino acids), containing polyglutamine domains exceeding the pathologic threshold of Q36, compared to httQ23 (90 amino acids). There was less aggregation of luciferase, a control protein containing 16 glutamines, but none in tandem. The aggregated huntingtin does not show green birefringence after staining with Congo Red, and thus cannot be considered to be amyloid.

In producing the results shown in FIG. 1B, RNA synthesized from the T7 promoter of pcDNA3 containing the httQ23 or httQ41 constructs were translated in the presence of $^{35}$S-Methionine in a rabbit reticulocyte lysate system, producing soluble products of the expected molecular weights (lanes 1 and 5, respectively). Incubation in the presence of increasing concentrations of transglutaminase produced increasing amounts of an aggregate that remained at the top of the 4.15% gradient gel (lanes 2–4 for httQ23 and lanes 6–8 for httQ41).

Figure 1C:
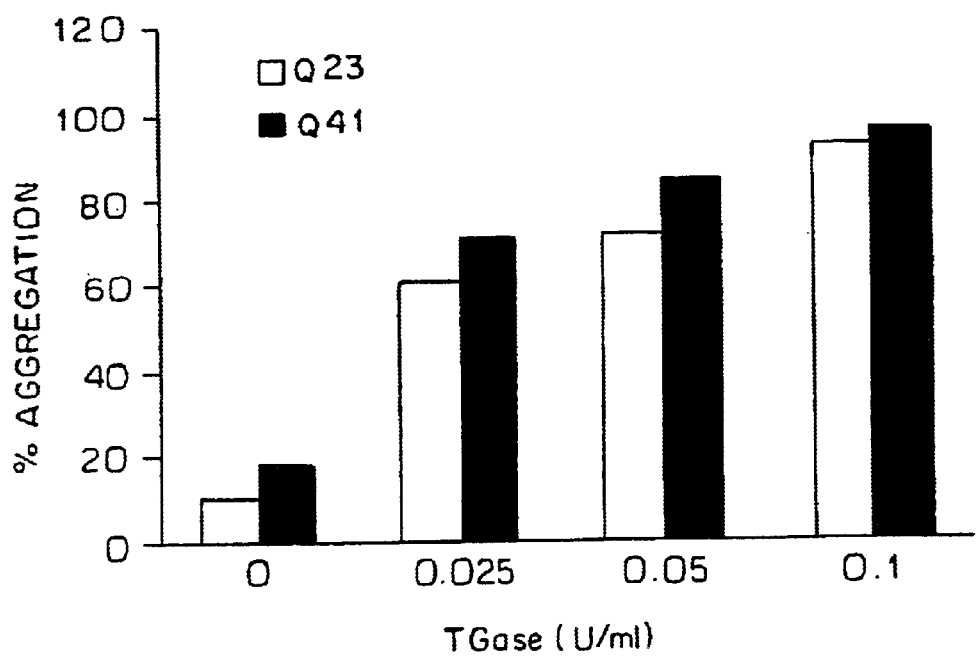
FIG. 1C shows quantitation of huntingtin aggregation in the presence of transglutaminase.
Figure 2B:
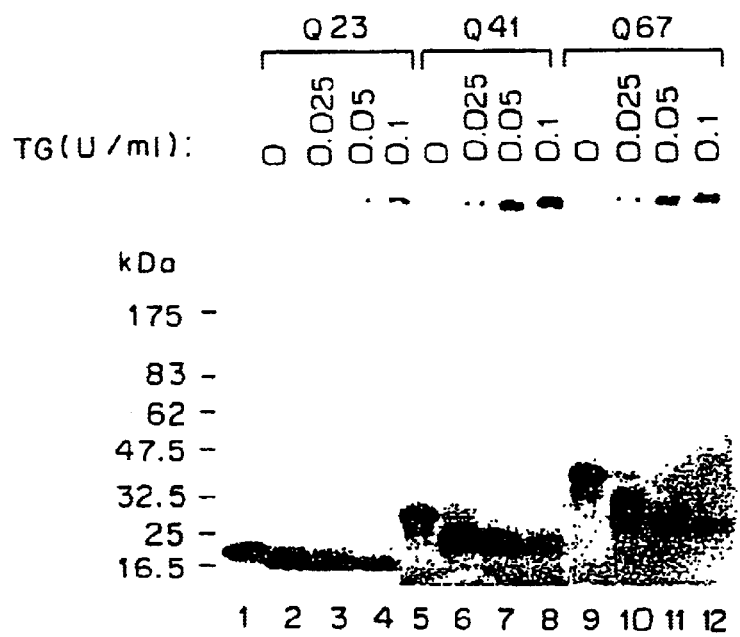
FIG. 2B shows in vitro expression of httQ23, httQ41 and httQ67.
Figure 2C:
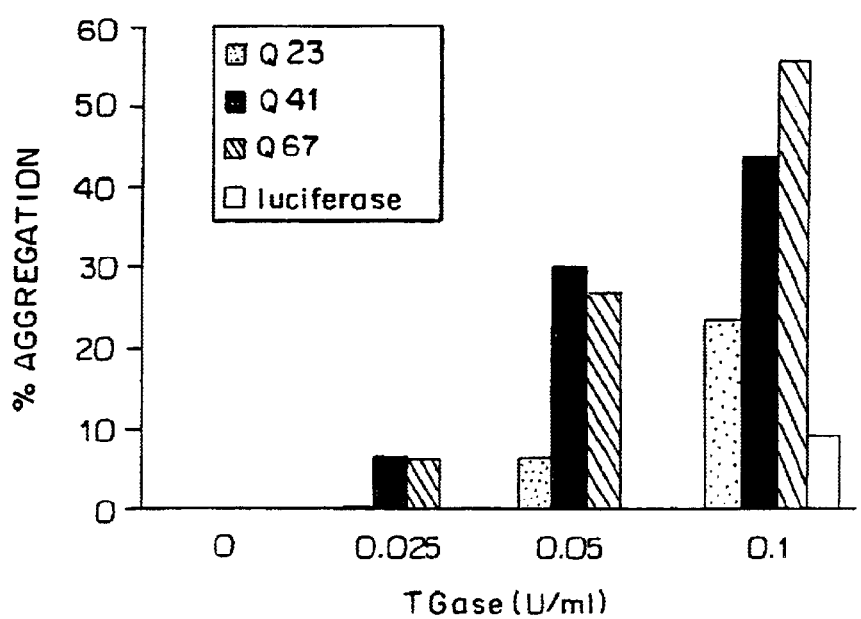
FIG. 2C shows quantitation of huntingtin aggregation in the presence of transglutaminase.

FIG. 1C shows the quantitation of htt aggregation in the presence of transglutaminase. Densitometry was performed on the gel in FIG. 1B. The percentage of products that remained at the top of the gel within each lane is shown as a function of transglutaminase concentration. There is no obvious difference in aggregation percentage between the two constructs.

Figure 1D:
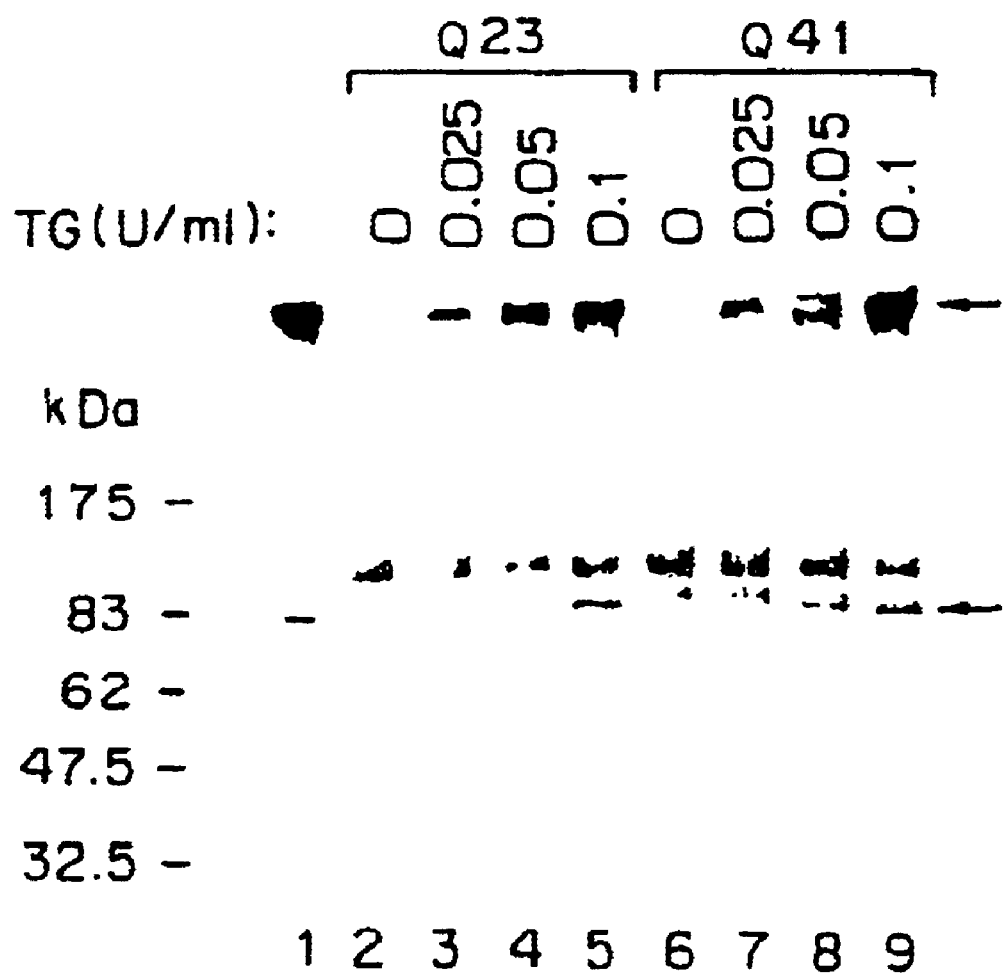
FIG. 1D illustrates how transglutaminase migrates with huntingtin aggregates.

Transglutaminase per se can be detected in the aggregates of either httQ41 or httQ23, as shown in FIG. 1D, using affinity purified anti-transglutaminase antibodies. On Western blot analysis with anti-transglutaminase antibodies, products are seen which co-migrate with the $^{35}$S labelled httQ23 or $^{35}$S labelled httQ41 aggregation (FIG. 1D, lanes 3–5 and 7–9). Interestingly, transglutaminase alone can cross-link itself, as shown in FIG. 1D, lane 1.

FIG. 1D illustrates that transglutaminase co-migrates with the htt aggregates. A parallel gel to that shown in FIG. 1B was blotted with an antibody against transglutaminase. Exposure times were such that none of the $^{35}$S-methionine labelled htt would be visible. The identities of the lanes are identical to that shown in FIG. 1A except for an additional lane containing 1 mU of transglutaminase alone (lane 1). The transglutaminase localized to the top of the 4–15% gradient gel (upper arrows), as did the htt aggregates in FIG. 1B. Transglutaminase alone migrated at the expected molecular weight of approximately 80 kDa (lower arrow), but, interestingly, also formed a higher molecular weight species at the top of the gel (lane 1). The staining found between the arrows is non-specific background, since it is also seen in the lanes without transglutaminase (lanes 2 and 6).

It should be noted that httQ23, httQ41 and httQ67 are all soluble, in comparison with htt fusion proteins produced in bacteria after the GST fusion proteins have been cleaved (Scherzinger et al, 1997). The in vivo translated material was found to be soluble when analyzed by SDS-PAGE after up to 125 hours of observation at room temperature. In contrast, GST fusion constructs of htt with Q>30 are insoluble after the GST protein is enzymatically cleaved. Clots consisting of GST are observed following partial enzymatic cleavage, and may serve as a nucleation factor for the aggregation of htt (Scherzinger et al, 1997).

FIG. 2A shows the constructs used in in vitro translation. Each construct is drawn approximately to scale, and the size of the amino acids is shown. Each construct begins with the amino terminal methionine of the htt protein. The dark bar indicates the location and size of the polyglutamine repeats.

FIG. 2B shows the in vitro expression of httQ23, httQ41, and httQ67. RNA synthesized from the T7 promoter of pcDNA3 containing the httQ23, httQ41, or httQ67 constructs were translated in the presence of $^{35}$S-methionine in a rabbit reticulocyte lysate system, producing soluble products of the expected molecular weights (lanes 1, 5, and 9, respectively). Incubation in the presence of increasing concentrations of transglutaminase produced increasing amounts of an aggregate that remained at the top of the 4–15% gradient gel (lanes 2–4 for httQ23, lanes 6–8 for httQ41, andlanes 10–12 for httQ67). With increasing concentration of transglutaminase, products with molecular weight smaller than the htt monomers were also seen. It is assumed that these are partial degradation products of the monomeric htt as a result of endogenous protease activity in the added transglutaminase.

FIG. 2C illustrates quantitation of htt aggregation in the presence of transglutaminase. Densitometry was performed on the gel in panel (B). The percentage of products that remained at the top of the gel within each lane is shown as a function of transglutaminase concentration. The aggregation of an unrelated control protein, luciferase, at a single concentration of transglutaminase is also shown. There is a 2–3 fold greater amount of aggregation of httQ41 and httQ67 compared to httQ23 at each concentration of transglutaminase. This result, using the smaller huntingtin constructs, is in contrast to that with the larger huntingtin constructs.

Transqlutaminase Activity is Increased in Huntington's Disease Brains and in Brains of Mice Transgenic for the Huntington's Disease Mutation Prior to the present invention, there has been no information on whether TGase activity is present in the Huntington's disease brain or in Huntington's disease brain nuclei. To determine whether an extract from a Huntington's disease brain contains transglutaminase activity, it was ascertained on Western blots that transglutaminase is seen in nuclei isolated from the brain of a Huntington's Disease patient (httQ63/httQ26) and from control brain, as well as from cytoplasm isolated from Huntington's Disease brains (httQ44/Q16; httQ63/Q26) and from control brain, FIG. 3.

Figure 3:
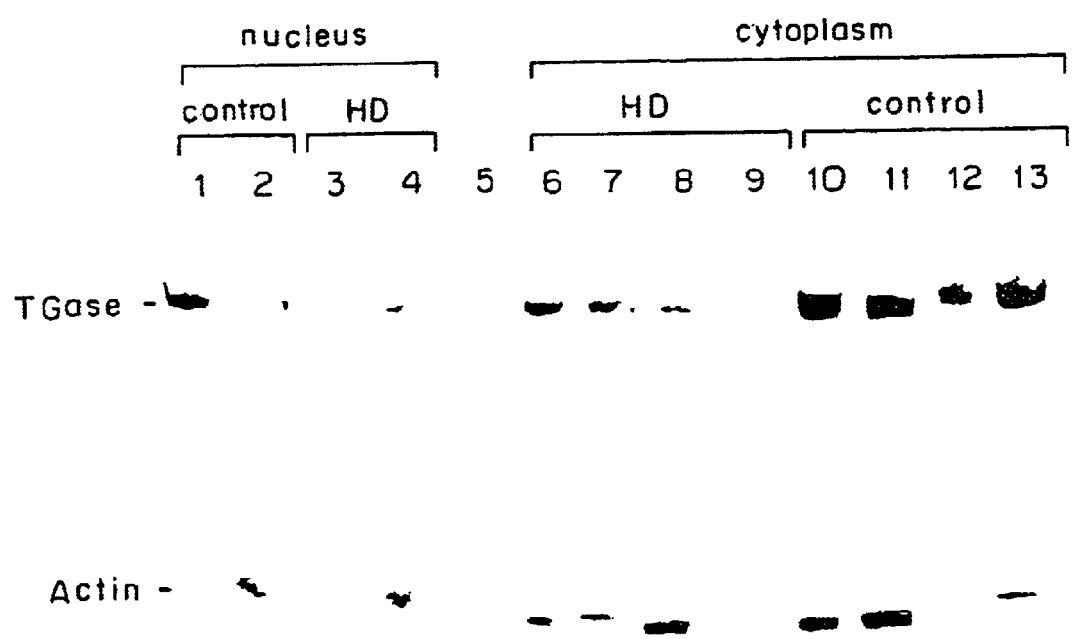
FIG. 3 shows transglutaminase in nuclei isolated from the brains of Huntington's Disease patients, as well as from control brains.

In FIG. 3, transglutaminase is seen in nuclei isolated from the brains of Huntington's Disease patients and from control brain, as well as from cytoplasm isolated from Huntington's Disease brains and from control brain. An 89 kDa band staining with anti-transglutaminase antibody, which migrates to the same position as recombinant guinea pig transglutaminase (data not shown), and a 42 kDa band staining with a monoclonal anti-actin antibody were seen in both nucleus and cytoplasm. Lanes 1 and 2 show control brain nuclear fraction, 50 and 100 µg of lysate. Lanes 3 and 4 show Huntington's disease brain nuclear fraction (httQ63/Q26), 50 and 100 µg, respectively. Lanes 8 and 9 are cytoplasmic extracts from Huntington's Disease brain (httQ44/Q16), 50 and 100 µg of lysate. Lanes 10 and 11 are cytoplasmic extracts from control brain, 50 and 100 µg of lysate. Lanes 12 and 13 are cytoplasmic extracts from another control brain, 50 and 100 µg of lysate.

Table 1 shows that a cytosolic extract from Huntington's Disease brain and from control brain provides enzymatic activity for the incorporation of radiolabelled putrescine, as an amine donor, into casein, which serves as an amine acceptor. This method for measuring brain transglutaminase was adapted from Folk and Cole (Folk et al, 1966). Casein serves as an excellent glutamine-containing protein substrate and a polyamide, while putrescine serves as the attacking nucleophile (Cooper et al, 1997). Enzymatic activity is completely inhibited by the transglutaminase inhibitor monodansyl cadaverine, as shown in Table 1. In the Huntington's Disease brain, in both the affected cortex andjin relatively unaffected areas like the cerebellum, which are affected in juvenile Huntington's Disease, transglutaminase activity was greater than in the corresponding areas of the control brain (HD cortex 14888±2864 cpm vs. normal cortex 6697±1410 cpm, mean ±1SEM, p<0.009 for HD cortex versus normal cortex; HD cerebellum 11221±2426 cpm vs. control cerebellum 2606±719 cpm, mean ±1SEM, p<0.001 for HD cerebellum versus control cerebellum.) Transglutaminase activity was also greater in extracts of nuclei from brains of Huntington's Disease patients than controls (HD brain cortical nuclear extract 6368±764 cpm vs. control brain cortical nuclear extract 2357±226 cpm, mean ±1SEM, Table 1).

TABLE 1

TGase Activity Is Increased in HD Brain

| Source of Brain Sample | + Casein | + Casein + MDC (n = 2) | − Casein | − Casein + MDC (n = 2) |
|---|---|---|---|---|
| a) HD Cortex | 14888 ± 2863* (n = 3) | 94 ± 18 | 464 ± 104 (n = 2) | 81 ± 17 |
| b) HD Cerebellum | 11221 ± 2426** (n = 3) | 186 ± 57 | 477 ± 61 (n = 2) | 58 ± 13 |
| c) Control Cortex | 6697 ± 1410# (n = 5) | 63 ± 10 | 607 ± 167 (n = 2) | 151 ± 39 |
| d) Control Cerebellum | 2606 ± 719 (n = 3) | 83 ± 14 | 145 ± 50 (n = 2) | 117 ± 30 |
| e) HD Corticular Nuclear Extract | 6368 ± 764## (n = 3) | ND | 153 ± 23 (n = 2) | ND |
| f) Control Corticular Nuclear Extract | 2357 ± 226 (n = 4) | ND | 189 ± 32 (n = 5) | ND |

TGase activities (CPM, mean ± SEM) were measured as described in the experimental procedures.
n = number of human patients analyzed
* = unpaired student's t test, p < 0.009 comparing a to c
** = p < 0.001 comparing b to d
# = p < 0.04 comparing c to d
## = p < 0.0001 comparing e to f
ND = Not Done In addition, transglutaminase activity in the brains of mice made transgenic for the Huntington's Disease mutation was investigated. Repeat sizes for the huntingtin transgene in the mice studied were Q149, Q147, Q148, Q156, Q154, Q150, and Q147, respectively. In Table 2, it can be seen that in the brains of mice made transgenic for the Huntington's Disease mutation, transglutaminase activity was significantly increased in the nuclear fraction compared to the nuclear fraction from control (HD mutant transgenic mice 7638±465 cpm vs. 6272±434 cpm, mean ±1SEM, p<0.04). In the cytoplasmic fraction there was no difference between mice with mutant Huntington's Disease transgenes and controls (cytoplasmic fraction from HD mutant mice 12213±662 cpm vs. control mice 11251±638 cpm, NS).

In both Huntington's Disease mutant transgenic mice and in control mice cytoplasmic transglutaminase activity was greater than nuclear transglutaminase activity (p<0.0001 for the HD mutant mice, as well as for the control mice), as shown in Table 2. In the human brain material, cytoplasmic transglutaminase activity was greater than nuclear transglutaminase activity in the control material (control brain cytoplasmic extract 6697±1410 cpm vs. control brain nuclear extract 2357±226, mean ±1SEM, p<0.001) and was just short of being significantly greater in the HD material as well (HD cytoplasmic extract 14888±2863 cpm vs. HD nuclear extract 6468±764, mean ±1SEM, p<0.07).

TABLE 2

TGase Activity Is Increased in Nucleus of Mice Transgenic for the HD Mutation

| Source of Brain Sample | TGase Activity (n = 8) |
|---|---|
| a) Nucleus HD | 7638 ± 465*/** |
| b) Cytoplasmic HD | 12213 ± 662 |
| c) Nucleus Control | 5272 ± 434*** |
| d) Cytoplasmic Control | 11251 ± 638 |

TGase activities (CPM, mean ± SEM) were measured as described in the experimental procedures.
n = number of mice analyzed
* = unpaired student's t test, p < 0.04 comparing a to c
** = p < 0.0001 comparing a to b
*** = p < 0.0001 comparing c to d Thus, it can be seen that TGase activity was elevated in the Huntington's Disease cortex and cerebellum regions where htt aggregates into nuclear inclusions. Moreover, TGase activity,was increased in Huntington's Disease brain nuclei. Interestingly, TGase activity was reduced in lymphoid cells from Huntington's Disease patients, a region where aggregates do not occur in Huntington's Disease. Regional differences in TGase activity might help to explain the exquisite anatomic localization of Huntington's Disease in the brain.

A recent study (Scherzinger et al., 1997) argued that amyloid formation could explain the nuclear inclusions in Huntington's Disease tissue. There are essential differences between the in vitro aggregates reported in this reference and the aggregates actually seen in neuronal nuclear inclusions in a Huntington's Disease brain (Igarashi et al., 1998) and in a spinocerebellar ataxia type 3 brain (Paulson et al., 1997). The aggregates formed in vitro after cleavage of GST as reported by Scherzinger et al. have the properties of amyloid, are able to stain with Congo red, and show green birefringence under polarized light. Congo red binding is characteristic of amyloid aggregates.

However, in the Huntington's Disease brain no amyloid inclusions have been reported, and it has been shown here that inclusions in the Huntington's Disease brain do not stain with Congo red and therefore should not be considered amyloid. Thus, neither TGase-catalyzed polymers of htt, as shown in FIGS. 1 and 2, nor the polymers that appear in Huntington's Disease tissue have the optical characteristics of amyloid. The covalent linkages to htt polymerized with TGase probably do not give enough order for the periodic binding of Congo red that is necessary for red-green birefringence. It is possible that, after purification, some degree of Congo red staining might be visible in aggregates if regions of the aggregates consist of proteins bound by polar zippers, but this is certainly not evident in tissue sections from the Huntington's Disease brain.

In contrast to Scherzinger's results, it was found that full-length htt, including htt with polyglutamine expansions in the pathologic range, does not aggregate in vitro without TGase. Short in vitro-translated fragments of 90 to 300 amino acids from the N terminus of htt and longer in vitro-translated portions of the N-terminal portion (50–60 kDa) of htt containing O91 do not aggregate in vitro.

One reason that the data are different can be attributed to the fact that the concentration of the translated protein was not high enough to start the aggregation process. It is known that a concentration of approximately 30 to 100 $\mu$M (Harper, 1997) is necessary for the formation of fibrillar aggregates. In yeast, for amyloid aggregates of prion protein above a concentration of 6 µM, the rate-limiting step in conversion from oligomers to aggregates is unaffected by protein concentration (DePace et al., 1998).

It was found that the degree of enzyme-catalyzed aggregation is a function of the size of the portions of htt outside the polyQ domain. There was an increased amount of aggregation with the constructs httQ41 (110 amino acids) and httQ67 (135 amino acids), which contained polyQ domains that exceed the pathologic threshold of Q36, compared with httQ23 (90 amino acids). This threshold is not observed for larger fragments of htt that exceed 300 amino acids. In Martindale et al. (1998), the degree of apoptosis and death in fibroblasts and the number of aggregates in monkey kidney cells and in cortical neuronal cultures was related to the size of the htt fragment domain. Perinuclear aggregates are also more frequent in COS cells transfected with truncated DRPLA protein that contain a pathological polyQ domain than they are with full-length DRPLA protein that contain a pathologic polyQ domain (Igarashi et al., 1998). In Saudou et al. (1998), shorter fragments of htt with a pathological polyQ domain formed aggregates more readily than longer fragments with a pathologic domain.

Inhibition of Transalutaminase Activity by Increasing Length of PolyQ in htt in Lymphoblastoid Lines Experiments were conducted to determine if there were a correlation between the number of glutamine repeats in huntingtin and transglutaminase activity in lymphoid cells. Investigators had previously shown that transglutaminase activity is decreased in lymphoid cells taken from Huntington's Disease patients (Cariello et al, 1996). Transglutaminase activity, which is elevated in Huntington's Disease brain, was contrasted to transglutaminase activity in non-neurologic tissue. Human EBV transformed lymphoblastoid diploid cell lines containing htt with various length of polyQ were used (Anderson et al, 1984). These cell lines contain tissue transglutaminase. The intrinsic transglutaminase activity in these cells was measured, and four diploid cell lines were used containing httQ18/httQ22, httQ70/httQ19, httQ46/httQ20, and httQ48/httQ41.

Figure 4:
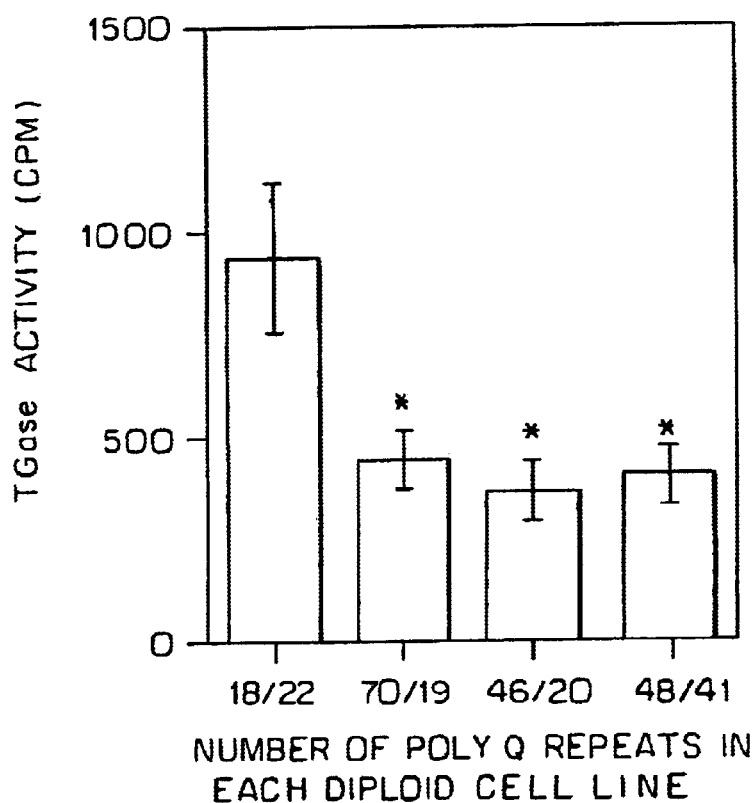
FIG. 4 shows the number of polyQ repeats in each diploid cell line from Huntington's Disease patients and a healthy control.

FIG. 4 shows that there is a negative correlation (p<0.03) between endogenous transglutaminase activity and the length of the polyQ stretch in huntingtin in the transformed cell lines. Thus, transglutaminase activity in lymphoblastoid cell lines is inhibited when the cell lines are derived from patients with Huntington's Disease, in contrast to transglutaminase activity in Huntington's Disease brain, which is elevated in comparison to control brain. Moreover, it appears that a single allele with polyQ of a certain length is sufficient to suppress transglutaminase activity.

In FIG. 4, four diploid cell lines contained httQ18/httQ22, httQ70/httQ19, httQ46/httQ20, and httQ48/httQ41. The number of polyQ repeats in the htt alleles is shown in the x-axis. This is a representative experiment from 6 repetitions, p<0.03, comparing Huntington's Disease lines to the control line.

From this, it can be concluded that gene therapy to suppress transglutaminase activity would be useful. Gene therapy treats these conditions by introducing into the appropriate cell DNA coding for the desired gene product. Gene therapy can be effected by any suitable means, including receptor mediated gene delivery, transkaryotic implantation, and viral shuttle vectors such as retroviral gene transfer. Many techniques have been used for gene therapy, including direct injection of non-infectious, non-oncogenic plasma DNA encapsulated in liposomes (Nicolau et al, 1983); immunoliposomes (Wang et al, 1987); and in a liposome/red blood cell membrane hybrid (Kaneda et al, 1989). Anderson (1984) reported that retroviral gene transfer offered high efficiency of infection, stable integration, and expression in most cells. In vivo gene therapy has been used for patients with ADA deficiency who have had reinfused into their blood autologous lymphocytes carrying the ADA gene, and in cancer patients with advanced melanoma, who have had reinfused tumor infiltrating lymphocytes which carry the gene for tumor necrosis factor (Rosenberg et al, 1980).

Viruses have been used to deliver DNA in gene therapy. Among the types of gene therapy in which viruses have been used for transfer are HSV-1 vector mediated transfer of BDNF into cerebellar granule cells, Alonso et al (1996); gene delivery to the heart and to cardiac myocytes and vascular smooth muscle cells using herpes virus vectors, Coffin et al (1996); neurotropic virus for treatment of Parkinson's Disease, Fink et al (1997); expression of the lacZ reporter gene in the rat basal forebrain, hippocampus, and nigrostraital pathway using a non-replicating herpes simplex vector, Maidment et al (1996).

Haynes et al (1996) reported on nucleic acid immunization involving the direct in vivo administration of antigen-inducing plasmid DNA molecules which produce microbial antigens at the site of DNA delivery. Krisky et al (1997), disclose that herpes simplex virus type 1 carries a large number of viral functions which can be replaced by foreign genes to create a vector for gene therapy applications.

Transfer of antisense transglutaminase activity or of a gene with normal transglutaminase activity via a retroviral vector can spare neurons from the toxic effect of expanded CAG proteins such as huntingtin in Huntington's Disease. Retroviral vectors are designed that would deliver the antisense transglutaminase gene to neurons and microglial cells expressing MHC class II, which does not occur in normal brain tissue. Transfer of transglutaminase via activated T cells which would recognize MHC class II on microglial cells could then replenish the enzyme in diseased brain.

Treatment of Autoimmune Disease

Transglutaminase is critical for adherence of activated lymphocytes to inflamed brain endothelium and for the subsequent passage of lymphocytes into the central nervous system in inflammatory diseases of the central nervous system. Consequently, administration of a transglutaminase inhibitor, in one case, monodansyl cadaverine, reversed paralytic disease in experimental autoimmune encephalomyelitis (EAE), which is an animal model of multiple sclerosis, and prevented the accumulation of inflammatory lymphocytes in the brain.

Paraparetic mice with experimental autoimmune encephalomyelitis were administered one dose of monodansyl cadaverine. Ongoing paralysis was reversed, as was histological evidenceof lymphocytic infiltration in brain. Mice treated in vivo with monodansyl cadaverine, a transglutaminase inhibitor, were apparently free of disease with no untoward side effects. Thus, diseases mediated in part by transglutaminase can be treated with transglutaminase inhibitors.

Figure 5:
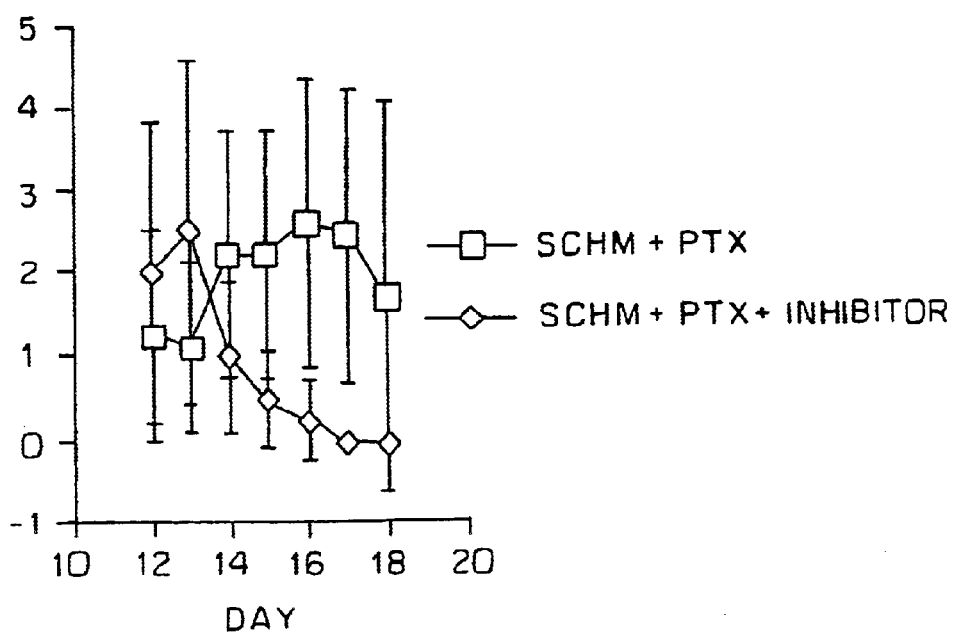
FIG. 5 shows the effects of transglutaminase inhibitor on EAE.

FIG. 5 shows the effect of administration of a transglutaminase inhibitor on EAE. 0.05 mM monodansyl cadaverine was injected intraperitoneally into one of two groups of mice. The injection was given on day 13 after induction of disease, marked in the FIG. by an arrow.

As can readily be seen in FIG. 5, a significant influence (p=0.03 compared to control) of the transglutaminase inhibitor occurs following the second day of its injection. The nonsignificant difference on days 17 and 18 are due to a natural remission of EAE. Mononuclear. cell infiltration was checked in brains by hematoxilin-eosin staining. Mice treated with monodansyl cadaverine showed high levels of infiltration while controls injected with the vehicle did not show any sign of infiltration.

Treatment of Experimental Autoimmune Encephalitis

Figure 6:
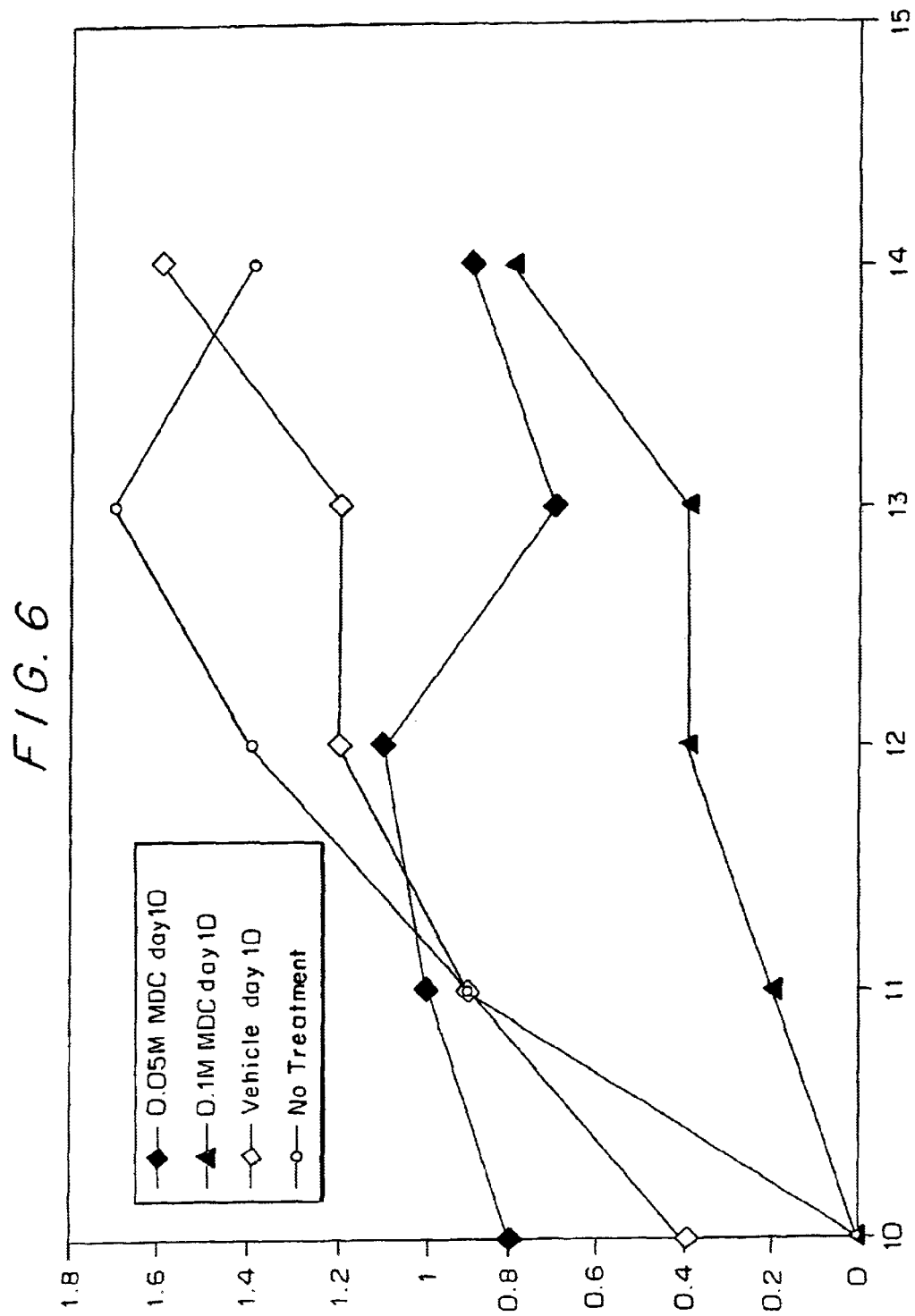
FIG. 6 shows the results of inhibiting EAE in mice with different concentrations of mono dansyl cadaverine.

FIG. 6 shows a comparison of varying concentrations of mono dansyl cadaverine with vehicle or no treatment. To obtain the data shown in FIG. 6, experimental autoimmune encephalitis (EAE) was induced in ten week old SJL female mice. EAE was induced by an injection of 4 mg of mouse spinal cord homogenate in 1 ml of CFA. The injections were given intradermally in three places (two places in the flanks and one in the neck). On the same day, day 1, and on day 2, an intraperitoneal injection of pertussis toxin was given. The mice were treated with different concentrations of mono dansyl cadaverine on day 10. One group was injected twice on days 7 and 10 with 0.05M mono dansyl cadaverine.

The grading score for EAE is 0, normal; 1, mild paraparesis; 2, paraparesis; 3, severe paraparesis; 4, quadriparesis; 5, dead.

Figure 7:
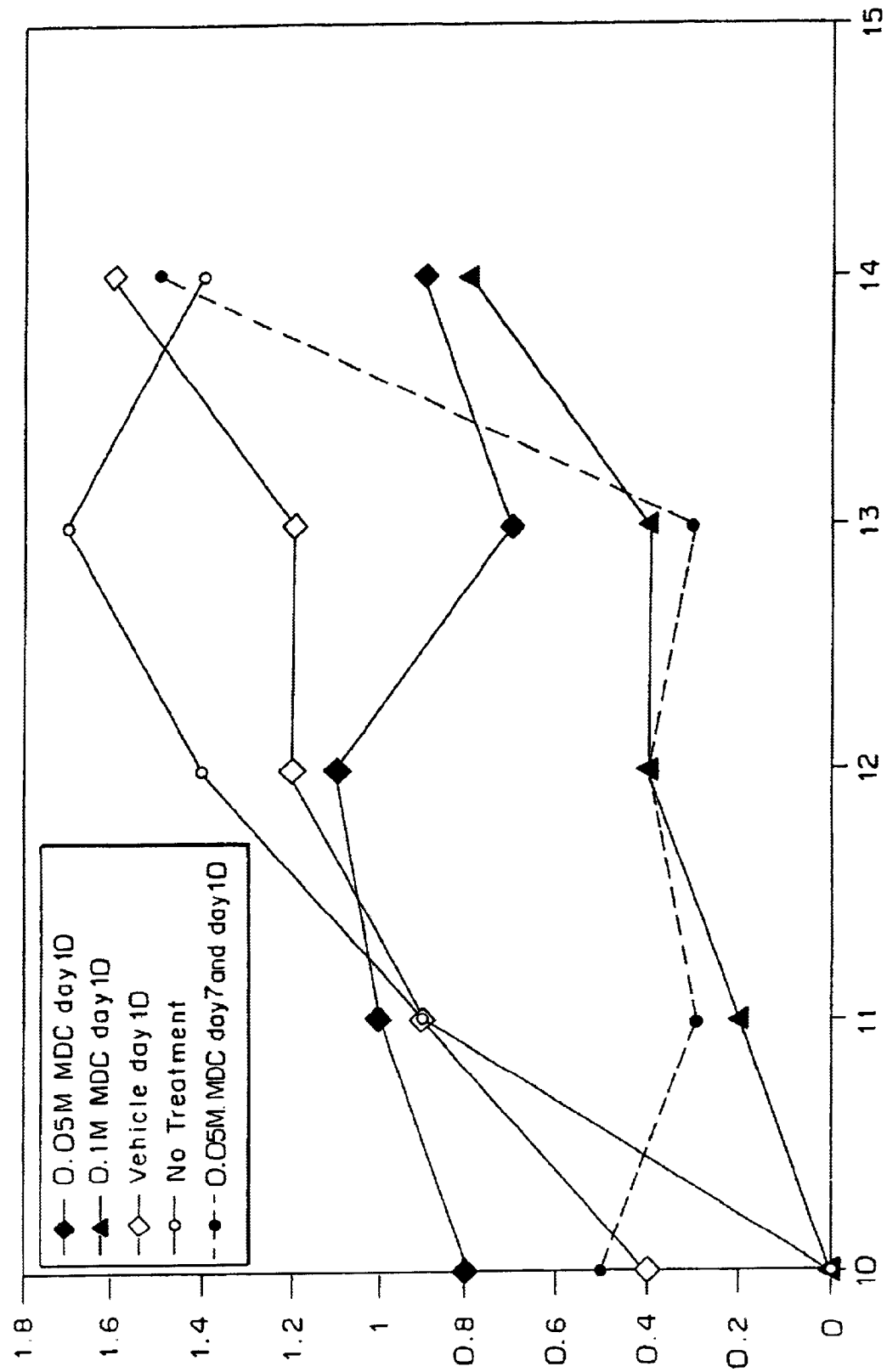
FIG. 7 shows the results of treating EAE in mice with different concentrations of mono dansyl cadaverine.

FIG. 7 shows a comparison of varying concentrations of mono dansyl cadaverine with vehicle or no treatment. To obtain the data shown in FIG. 7, experimental autoimmune encephalitis (EAE) was induced in ten week old SJL female mice by an injection of 4 mg of mouse spinal cord homogenate in 1 ml of CFA. The injections were given intradermally in three places (two places in the flanks and one in the neck). On the same day, day 1, and on day 2, an intraperitoneal injection of pertussis toxin was given. The mice were treated with different concentrations of mono dansyl cadaverine on day 10. One group was injected twice on days 7 and 10 with 0.05M mono dansyl cadaverine.

In both FIGS. 6 and 7, the y axis is the score of the disease, with higher scores indicating greater severity of disease.

Pharmaceutical compositions for administration according to the present invention can comprise at least one transglutaminase inhibitor according to the present invention in a pharmaceutically acceptable form optionally combined with a pharmaceutically acceptable carrier. These compositions can be administered by any means that achieve their intended purposes. Amounts and regimens for the administration of a composition according to the present invention can be determined readily by those with ordinary skill in the art of treating neurodegenerative diseases and other diseases mediated by transglutaminase activity. Where the transglutaminase inhibitor must be administered to the cell nucleus, specific molecules such as polyarginine, which target the cell nucleus, can be used to deliver the transglutaminase inhibitor to the intended site. However, any known method an be used for targeting the active ingredient to the cell nucleus.

Pharmaceutical compositions for administration according to the present invention can comprise at least one transglutaminase inhibitor in a pharmaceutically acceptable form, optionally combined with a pharmaceutically acceptable carrier. These compositions can be administered by any means that achieve their intended purposes. Amounts and regimens for the administration of a transglutaminase inhibitor for treating neurological and inflammatory diseases mediated by transglutaminase activity according to the present invention can be determined readily by those with ordinary skill in the art of treating these diseases.

For example, administration can be by parenteral, such as subcutaneous, intravenous, intramuscular, intraperitoneal, transdermal, or buccal routes. Alternatively or concurrently, administration can be by the oral route, transdermally, transmucosally, or rectally. While oral dosage is preferred, administration by suppositories may be useful. The dosage administered depends upon the age, health and weight of the recipient, type of previous or concurrent treatment, if any, frequency of the treatment, and the nature of the effect desired.

Compositions within the scope of this invention include all compositions comprising at least one transglutaminase inhibitor in an amount that is safe and effective to achieve its intended purpose. While individual needs vary, determination of optimal ranges of effective amounts of each component is within the skill of the art. Typical dosages can comprise from about 0.0001 to about 100 mg/kg body weight daily.

The effective amounts of agents for inhibiting transglutaminase activity can be readily determined. The presently preferred daily dosage is between about 1 microgram and about 100 grams of the active agent. Of course, the actual preferred amount of agent to be administered varies according to the particular form of the agent, whether it is the agent per se or an analog thereof, the particular composition formulated, and the mode of administration.

Administration can be conducted continuously or periodically within the maximum dose tolerated by the individual patient. Of course, optimal administration rates for a given set of conditions can be ascertained by those skilled in the art using conventional dosage administration tests.

The compounds of the present invention can be administered in the form of pharmaceutically acceptable compositions, that is, with the active ingredient mixed with or encapsulated in a pharmaceutically acceptable carrier. Compositions within the scope of the invention thus include compositions wherein the active component is present in an effective amount to achieve its intended purpose. Determination of the effective amounts is well within the skill in the art.

In addition to the compounds of the present invention, these pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered orally and which can be used for the preferred type of administration, such as tablets, dragees and capsules, and also preparations which can be administered rectally, such as suppositories, as well as suitable solutions for administration by injection or orally, contain from about 0.1 to 99%, and preferably from about 1–85% of the active ingredient, together with a suitable excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding a resulting mixture, and processing the mixture of granules, after adding suitable auxiliaries, if desired or necessary, to obtain tablets of dragee cores.

Examples of suitable excipients include lactose, sucrose, mannitol, sorbitol, cellulose preparations, calcium phosphates, binders, such as starch paste from maize starch, wheat starch, rice starch, potato starch, gelatin, tragacanth, methyl cellulose, hydropropylmethlycellulose, sodium carboxymethylcellulose and/or polyvinyl pyrrolidone. If desired, disintegrating agents may be added, such as the above-mentioned starches, as well as carboxymethyl starch, cross-linked polyvinyl pyrrolidone, agar, alginic acid, sodium alginate, and the like.

Auxiliaries include flow-regulating agents and lubricants, such as silica, talc, stearic acid or salts thereof and/or polyethylene glycol. Dragee cores are provided with suitable coatings which, if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures.

In order to produce coatings resistant to gastric juices, solutions of suitable cellulose preparations, such as acetyl cellulose phthalate or hydroxypropylmethyl cellulose phthalate are used. Dyestuffs or pigments may be added to the tablets or dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer, such as glycerol or sorbitol. The push-fit capsules can contain the active compounds in the form of granules which may be mixed with filler, such as lactose, binder, such as starches, and/or lubricants, such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Suitable formulations of parenteral administration include aqueous suspensions of the active ingredients, as well as appropriate oily injection suspensions. Suitable lipophilic vehicles include fatty oils such as sesame oil, or synthetic fatty acid esters, such as ethyl oleate or triglycerides. Aqueous injection suspensions may contain substances which increase the viscosity of the suspension, such as sodium carboxymethyl cellulose, sorbitol and/or dextran. Optionally, the suspension may also contain stabilizers.

The compounds of the present invention may be administered in a variety of convenient forms, orally, parenterally, rectally, or percutaneously to treat dementia. The dosage required for each patient may vary widely, depending upon the degree of neurological damage and the individual patient response. However, in general, a dosage of from about 0.001 to about 100 mg/kg of body weight is appropriate for most patients.

For example, administration can be by parenteral, such as subcutaneous, intravenous, intramuscular, intraperitoneal, transdermal, or buccal routes. Alternatively or concurrently, administration can be by the oral route. The dosage administered depends upon the age, health and weight of the recipient, type of previous or concurrent treatment, if any, frequency of the treatment, and the nature of the effect desired.

As discussed above, gene therapy can be used to suppress transglutaminase activity by introducing into the appropriate cell DNA coding for the normal gene product. Gene therapy can be effected by any suitable means, including receptor mediated gene delivery, transkaryotic implantation, and viral shuttle vectors such as retroviral gene transfer.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps. for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

References

Alonso et al, *Neuro Report* 7(18):3105 (1996).
Anderson, *Science* 226:401 (1984).
Anderson et al, *In Vitro* 20:856–858 (1984).
Becher et al., *Neurobiol. Dis.* 4:387–397 (1998).
Burke et al, *Nature Medicine* 2:347–350 (1996).
Cariello et al, *Human Genetics* 98:633–635 (1996).
Ciechanover, A., *Cell* 79:13–21 (1994).
Ciechanover et al, *Proc. Natl. Acad. Sci. (USA)* 95:2727–2730 (1998).
Coffin et al, *Gene Therapy* 3(7):560 (1996).
Cooper et al, *J. Neurochem.* 69:431–434 (1997).
Curtis et al., *Methods Enzymol.* 45: 177–191 (1976).
Davies et al, *Cell* 90:537–548 (1997).
DePace et al., *Cell* 93:1241–1252 (1998).
Dietrich et al, *Nature Medicine* 7:797–801 (1997).
DiFiglia et al, *Science* 277:1990–1993 (1997).
Ebens et al, *Cell* 74:15–27 (1993).
Encinas et al, *Nature Genetics*, 21:158–160 (February, 1999).
Fink et al, *Experimental Neurolocy* 144(1):103 (1997).
Folk, E. J., *Ann. Rev. Biochem.* 49:517–531 (1980).
Folk et al, *Biochim. Biophys. Acta* 122:244–264 (1966).

Glenner, G. G., *New England Journal of Medicine* 302:128301292 and 1333–1343 (1980).
Goldberg et al, *Nat. Genet.* 13:442–449 (1996).
Green, H., *Cell* 74:955–956 (1993).
Greenberg et al, *FASEB J* 5:3071–3077 (1991).
Harper et al *Ann. Rev. Biochem.* 66:385–407 (1997).
Haynes et al, *J. Biotechnol.* 44(1–3):37 (1996).
Huntington, G., *Medical and Surgical Resorter. Philadelphia* 26:317–321 (1872).
Huntington's Disease Collaborative Research Group, *Cell* 72:9791–983 (1993).
Igarashi et al, *Nature Genet.* 18:111–117 (1998).
Jarrett et al, *Cell* 73:1055–1058 (1993).
Johnson et al., *Brain Res.* 751:323–329 (1997).
Kahlem et al, *Proc. Natl. Acad. Sci. (USA)* 93:14580–14585 (1996).
Kahlem et al, *Molecular Cell* 1:595–601 (1998).
Kaneda et al, *Science* 243:375 (989).
Kim et al, *J. Investigative Dermatolocy* 103:137 (1994).
Krisky et al, *Gene Therapy* 4(10):1120 (1997).
Lesort et al., *J. Biol. Chem.* 273:11991–11994 (1998).
Li et al, *Nature* 378:398–402 (1995).
Lorand, L., *Proc. Natl. Acad. Sci. (USA)* 93:14310–14313 (1996).
Lunkes et al, *Nature Medicine* 3:1201–1202 (1997).
Maidment et al, *Experimental Neurolocy* 139(1):107, (1996).
Mangiarini et al, *Cell* 87:493–506 (1996).
Martindale et al., *Nat. Genet.* 18:150–154 (1998).
Matilla et al, *Nature* 389:974–976 (1997).
Mosher, F. D., *Molecular and Cellular Biochem.* 58:63–68 (1984).
Nicolau et al, *Proc. Natl. Acad. Sci. (USA)* 80:1068 (1983).
Ordway et al, *Cell* 91:753–763 (1997).
Paulson et al, *Neuron* 19:333–344 (1997).
Persichetti et al, *Mol. Med.* 1:374–383 (1995).
Perutz, M. F., *Cur. Opin Struct. Biol.* 6:848–858 (1996).
Perutz et al, *Proc. Natl. Acad. Sci. (USA)* 91:5355–5358 (1994).
Portera-Caillau et al, *J. Neuroscience* 15:3775–3787 (1995).
Prusiner et al, *Cell* 35:349–358 (1983).
Robitaille et al., *Brain Pathol.* 7: 901–926 (1997).
Robbins, S. L., Patholoy, W B Saunders (Philadelphia, 1967), pp. 219–227.
Rosenberg et al, *N. Ens. J. Med.* 323:570 (1980).
Ross, C. A., *Neuron* 15:493–496 (1995).
Saudou et al., *Cell* 95:55–66 (1998).
Scherzinger et al, *Cell* 90:549–558 (1997).
Schilling et al, *Hum. Mol. Genet.* 4:1365–1371 (1995).
Sharp et al, *Neuron* 14:1065–1074 (1995).
Skinner et al, *Nature* 389:971–973 (1997).
Steinman, L., *Cell* 80:7–10 (1995).
Stott et al, *Proc. Natl. Acad. Sci. (USA)* 92:6509–6513 (1995).
Strong et al, *Nature Genet.* 5:259–265 (1993).
Tarasca et al, *Analvtical Biochemistry* 186:135–140 (1990).
Trottier et al, *Nature Genet.* 10:104–110 (1995).
Wang et al, *Proc. Natl. Acad. Sci.* 84:7851 (1987).
Zhao, et al., *Cell* 95:625–636 (1998).

What is claimed is:

1. A method of treating a disease mediated by transglutaminase, comprising administering to a patient in need thereof an effective amount of a transglutaminase inhibitor selected from the group consisting of monodansyl cadaverine, cystamine, putrescine, a monoamine, a diamine, gamma-amino benzoic acid, N-benzyloxy carbonyl, 5-deazo-4-oxonorvaline p-nitrophenylester, glycine methyl ester, $CuSO_4$, and tolbutamide, wherein the disease is selected from the group consisting of Huntington's Disease, spinobulbar atrophy, spinocerebellar ataxia, Machado-Joseph disease, and dentatorubralpallidoluysian atrophy.

2. The method of claim 1, wherein the transglutaminase inhibitor is monodansyl cadaverine.

3. The method of claim 1, wherein the transglutaminase inhibitor is cystamine.

4. The method of claim 1, wherein the transglutaminase inhibitor is putrescine.

5. The method of claim 1, wherein the transglutaminase inhibitor is gamma-amino benzoic acid.

6. The method of claim 1, wherein the transglutaminase inhibitor is N-benzyloxy carbonyl.

7. The method of claim 1, wherein the transglutaminase inhibitor is 5-deazo-4-oxonorvaline p-nitrophenylester.

8. The method of claim 1, wherein the transglutaminase inhibitor is glycine methyl ester.

9. The method of claim 1, wherein the transglutaminase inhibitor is $CuSO_4$.

10. The method of claim 1, wherein the transglutaminase inhibitor is tolbutamide.

11. The method of claim 1, wherein the disease is Huntington's Disease.

12. The method of claim 1, wherein the disease is spinobulbar atrophy.

13. The method of claim 1, wherein the disease is spinocerebellar ataxia.

14. The method of claim 1, wherein the disease is Machado-Joseph disease.

15. The method of claim 1, wherein the disease is dentatorubralpallidoluysian atrophy.

* * * * *

UNITED STATES PATENT AND TRADEMARK OFFICE
CERTIFICATE OF CORRECTION

PATENT NO.         : 6,794,414 B1
APPLICATION NO. : 09/719770
DATED                 : September 21, 2004
INVENTOR(S)        : Steiman et al.

It is certified that error appears in the above-identified patent and that said Letters Patent is hereby corrected as shown below:

On the Title Page, in section 12, the name of the inventor should read --Steinman et al.--.

On the Title Page, in section 75, insert the following additional inventor information:

--Marcella Karpuj, San Francisco, CA (US) --.

Signed and Sealed this

Thirtieth Day of October, 2007

JON W. DUDAS
*Director of the United States Patent and Trademark Office*